United States Patent [19]
Sicurelli et al.

[11] Patent Number: 6,162,202
[45] Date of Patent: Dec. 19, 2000

[54] FLEXIBLE SYRINGE NEEDLE

[76] Inventors: Robert Sicurelli, 210 Circle Rd., Muttontown, N.Y. 11791; Samuel Masyr, 415 Bay Ridge Pkwy., Brooklyn, N.Y. 11209

[21] Appl. No.: 09/178,931
[22] Filed: Oct. 26, 1998
[51] Int. Cl.$^7$ .................................................. A61M 5/32
[52] U.S. Cl. ........................... 604/272; 604/264; 604/525
[58] Field of Search .............................. 604/13, 170, 264, 604/525, 272–275, 523, 268, 0.01–0.03

[56] References Cited

U.S. PATENT DOCUMENTS

| | | | |
|---|---|---|---|
| 3,884,230 | 5/1975 | Wulff | 128/221 |
| 4,018,222 | 4/1977 | McAleer et al. | 128/216 |
| 4,026,025 | 5/1977 | Hunt . | |
| 4,274,555 | 6/1981 | Sneider | 222/107 |
| 4,431,426 | 2/1984 | Groshong et al. | 604/280 |
| 4,512,769 | 4/1985 | Kozam et al. | 604/209 |
| 4,702,260 | 10/1987 | Wang | 128/753 |
| 4,735,619 | 4/1988 | Sperry et al. | 604/208 |
| 5,127,831 | 7/1992 | Bab | 433/80 |
| 5,544,651 | 8/1996 | Wilk | 128/633 |
| 5,910,133 | 6/1999 | Gould | 604/164 |

*Primary Examiner*—Sharon Kennedy
*Assistant Examiner*—Kevin C. Sirmons
*Attorney, Agent, or Firm*—Alfred M. Walker

[57] ABSTRACT

A flexible irrigation syringe tip with a "Luer Lock" or other type of connector commonly used in medical tubing includes a flexible needle. The needle shaft is preferably made of a material which is bendable but which returns to its original shape, such as silicone, polypropylene or other flexible metal alloys and has an open or a closed tip. The tip may be flat or rounded. The hollow shaft of the flexible syringe itself is parallel sided with at least one hole in it to allow the irrigation solution to flush the canal when inserted. Preferably, to insure backflowing of the fluid from the tip area of the syringe needle backwards up the tooth canal, the at least one hole is a lateral side port, which lateral port causes the exiting of fluid in a direction transverse to the longitudinal axis of flexible syringe needle. The shaft may have at least one fluid diverter, such as a flute or groove to help direct the debris up and out of the tooth. This flute or groove may be straight or spiraled. The shaft may also have at least one hatch marking or inscription to show length from tip towards the hub interface of the flexible syringe needle with the connector to the handle. The flexible irrigator syringe needle may be alternatively attached to a precision microprocessor fluid dispensing device to limit the pressure and temperature of application and the amount of fluid therethrough.

42 Claims, 7 Drawing Sheets

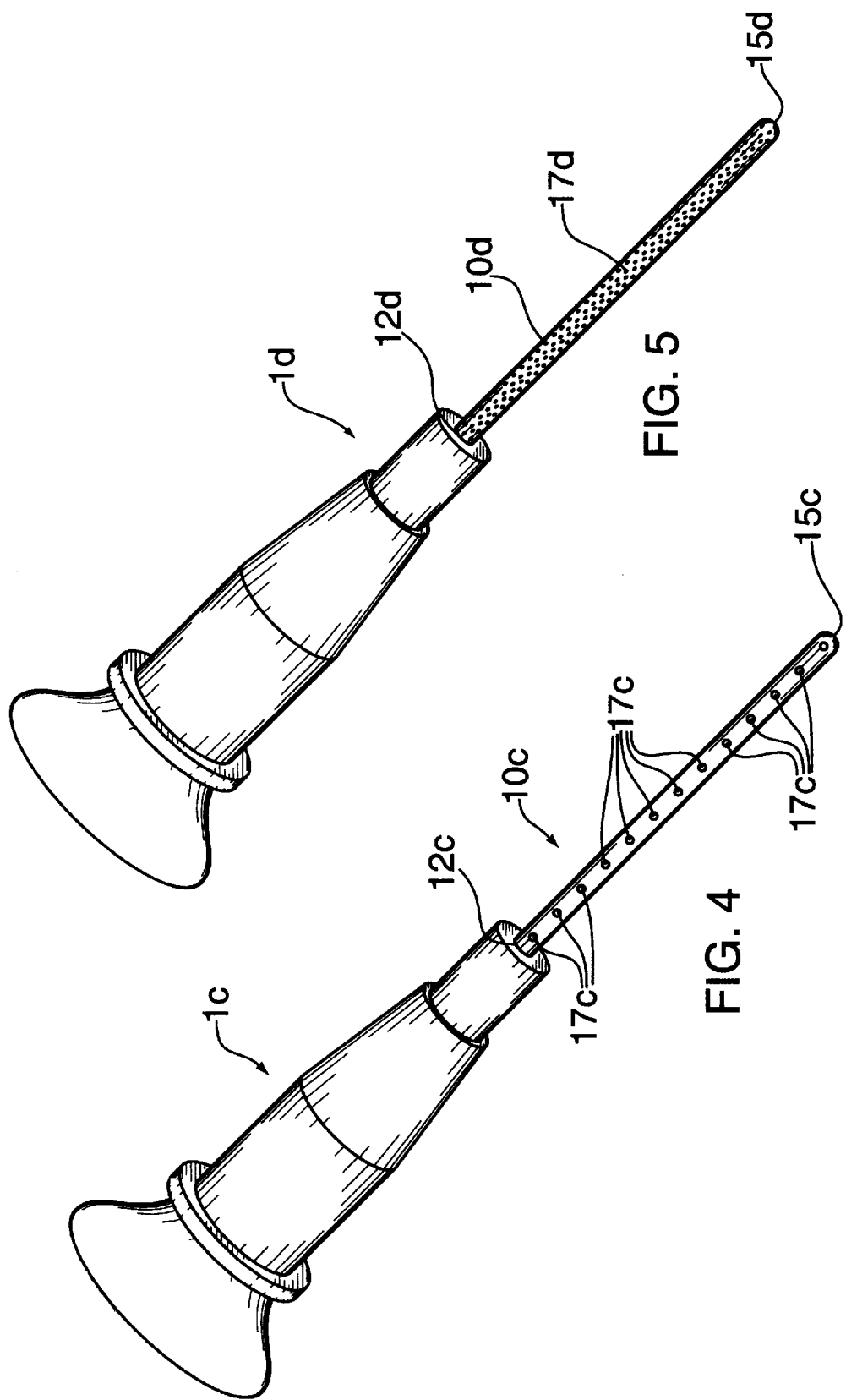

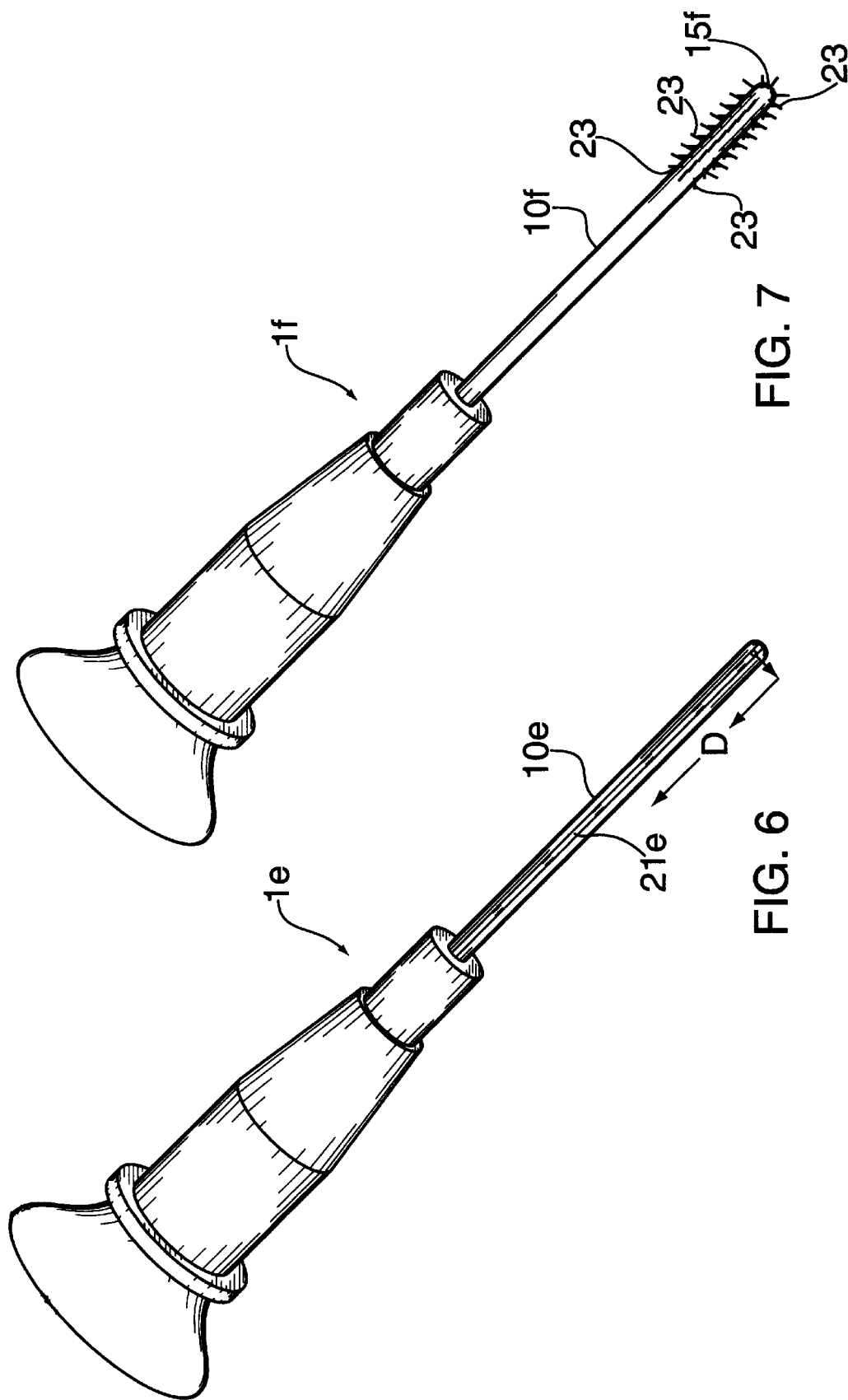

FLEXIBLE SYRINGE NEEDLE

FIELD OF THE INVENTION

The present invention relates to a flexible syringe needle for insertion into a body cavity, such as a tooth canal, during medical or dental treatment, such as, for example endodontic dental treatment.

BACKGROUND OF THE INVENTION

Endodontic therapy consists of filing and shaping the canal with instruments such as files, reamers, etc. This process produces shavings and debris made up of dentin and soft tissue (vein, nerve and capillary which makes up "pulp"). To prevent compacting and clogging of the canal with debris, it is necessary to irrigate the canal to keep it clean.

Traditionally the irrigation is done with a rigid irrigator tip made of metal, such as a hypodermic needle in various diameters. The problem with this is that the rigid metal or plastic tubes cannot negotiate to the end of the canal especially if the canal is curved. Also, the rigid metal end/plastic end has an edge which serves to bind the canal walls which can gouge and prevent adequate access. Another problem is that the opening at the end directs the pressure outward toward the apex of the root which can send debris and or irrigation fluid beyond the apex and into soft tissues causing medical complications.

Outside of the medical and dental field, flexible silicone needles of Technitool Company include hollow, flexible silicone needles for dispensing lubricating fluids to computer components.

Moreover, various attempts have been made to provide flexible fluid delivery conduits with discharge ports in the medical and dental field. Among these devices include U.S. Pat. No. 5,127,831 of Bab for a dental irrigation probe having a flexible tube attached to a rigid curved handle for forcibly delivering fluid between the outer periodontal surfaces of teeth, not within definitive body cavities, such as canals within the teeth. In Bab '831 the fluid is directed out axially through the probe.

U.S. Pat. No. 4,512,769 of Kozam describes a flexible needle having a single axially aligned fluid discharge port for cleaning between the teeth not necessarily within a definitive body cavity, such as a tooth canal. It includes a semi-rigid conical nozzle member at the fluid discharge end.

U.S. Pat. No. 4,702,260 of Wang describes a flexible bronchoscopic needle for retrieval of body tissues and body fluids therethrough. It includes a rigid needle attached to a flexible conduit. However, it is used to retrieve bodily fluids, and tissues, not to irrigate or provide medicine to a definitive body cavity, such as a tooth canal.

U.S. Pat. No. 4,735,619 of Sperry describes a rigid needle attached to a flexible conduit for intravenous introduction of fluids to the body. Since, the needle is not flexible, it may lodge against the walls of a tooth canal and break it, and it can't negotiated curved canals.

U.S. Pat. No. 4,274,555 of Sneider describes a feminine douche applicator with a hollow nozzle having lateral side ports for delivery of fluid therefrom. However, the applicator in Sneider is not on a scale of size for use within a tooth canal.

U.S. Pat. No. 3,884,230 of Wulff a flexible needle aiming device comprising a rigid needle within a helical spring member for aiming the needle properly to an injection site upon the skin of a recipient of fluids therefrom. However, Wolff '230 is inflexible and can't negotiate curved tooth canals.

Furthermore, U.S. Pat. No. 4,026,025 of Hunt descibes an air powered fluid delivery nozzle for thrusting a fluid and air mix or just air forcefully therefrom into the intraoral mouth cavity of a dental patient. In Hunt '025 the nozzle is inflexible and the fluid is directed out axially through the nozzle. The nozzle is not on a scale of size for use within a tooth canal.

Therefore, the aforementioned prior art devices are not suitable for intra-canal irrigation of a tooth during endodontic treatment.

OBJECTS OF THE INVENTION

It is an object of the present invention to provide an endodontic flexible syringe needle for irrigating and delivering medication to a definitive body cavity, such as an intra-tooth canal.

It is also an object of the present invention to provide an irrigator to irrigate the tooth canal to keep it clean.

It is also an object of the present invention to prevent compacting and clogging of the tooth canal with debris.

It is also an object of the present invention to provide a flexible needle to negotiate to the end of the tooth canal, especially if the canal is curved.

It is also an object of the present invention to prevent flow of debris and/or irrigation fluid beyond the apex of the tooth canal and into soft tissues, causing medical complications.

It is yet another object to provide a flexible fluid conducting needle with a laterally placed discharge port.

It is yet another object of the present invention to provide a collapsible fluid-inflatable elongated dispensing needle, which assumes its shape when filled with fluid.

It is yet another object to provide an electronic delivery system with a flexible needle, to push irrigation fluids and chemicals through the flexible needle.

It is also an object to provide irrigation fluids to a tooth canal at varied temperature, pressure and flow rates.

SUMMARY OF THE INVENTION

To improve on the disadvantages of the prior art, the present invention is a flexible irrigation syringe tip with a "Luer Lock" or other type of connector commonly used in medical tubing. The shaft is preferably made of silicone, polypropylene or other spring-type metal alloys, such as nitinol and others, and in a preferred embodiment has a closed tip. The tip may be flat or rounded. The diameters of the hollow shaft may range in predetermined I.S.O. conventional diameters that approximate the files and reamers that are used to file and shape the tooth canal to be endodontically treated.

The flexible syringe needle is made of a flexible needle material with a bendable memory therein. Therefore, the flexible syringe needle flexes back and is deformable from a first predetermined configuration such as a straight or curved shape, during insertion into a curved body cavity, such as a tooth canal. Because of the bendable memory, it flexes back and returns to the predetermined shape upon removal from the body cavity.

The hollow shaft of the flexible syringe itself is parallel sided with at least one hole in it to allow the irrigation solution to flush the canal when inserted. Preferably, to insure backflowing of the fluid from the tip area of the syringe needle backwards up the tooth canal, the at least one hole is a lateral side port, which lateral port causes the exiting of fluid in a direction transverse to the longitudinal axis of flexible syringe needle. The shaft may have at least one fluid diverter, such as a flute or groove to help direct the debris up and out of the tooth. This flute or groove may be straight or spiraled. The shaft may also have at least one hatch marking or inscription to show length from tip towards the hub interface of the flexible syringe needle with the connector to the handle, such as the Luer lock.

The shaft of the flexible needle syringe may have at least one bristle fibre or other attachment to facilitate a scrubbing action.

The shaft may also have at least one hole directed at an angle and in sequence with others to create a swirling action to help remove debris.

The flexible syringe needle can be color coded for I.S.O. instrumentation, such as, for example:

| | |
|---|---|
| Blue | .30 mm tip |
| Red | .25 mm tip |
| Yellow | .20 mm tip |
| White | .15 mm tip |
| Black | .40 mm tip etc. |

The flexible irrigator syringe needle may be alternatively attached to a precision microprocessor fluid dispensing device to limit the pressure of application and the amount of fluid therethrough. This embodiment may be used in conjunction with a foot or finger valve dispenser or flat touch pad input and output control panels that are easily sterilized and sanitized. The flexible irrigator syringe needle are disposable and may be sized smaller to provide easier movement.

Heat controls to regulate temperature and activate chemicals, such as, for example, chelating agents, are also used.

Pressure controls may be optionally added, since if fluid is applied through the flexible syringe needle under too much pressure, fluid may be expressed out through the apex of the tooth canal and into the surrounding tissues, if there is too much fluid flow power from the instrumentation, and the apex is open. Increasing the pressure may also be necessary to allow adequate flow in smaller diameter needles. If the user extends a needle beyond the apex of the tooth canal without knowing of this, damage to the soft and hard tissues below the apex may occur.

While the present invention is designed to be used for intra-canal irrigation of the interior of a tooth canal, it may also be used to introduce fluids or medicine into body cavities, such as a vascular blood vessel or vessels during vascular surgery, or into foramina holes in bones during bone surgery, or to negotiate within body cavities around rigid surfaces of bones or artificial steel plates during orthopedic surgery.

DESCRIPTION OF THE DRAWINGS

The present invention can best be described in conjunction with the accompanying drawings in which:

FIG. 4 is a closeup detail view of another embodiment for a flexible needle with longitudinally extending ports;

FIG. 5 is a closeup detail view of another embodiment for a flexible needle with micropores;

FIG. 6 is a closeup detail view of another embodiment for a flexible needle with a low directing channel;

FIG. 7 is a closeup detail view of another embodiment for a flexible needle with an axial discharge port;

DETAILED DESCRIPTION OF THE PREFERRED EMBODIMENTS

Figure 1:
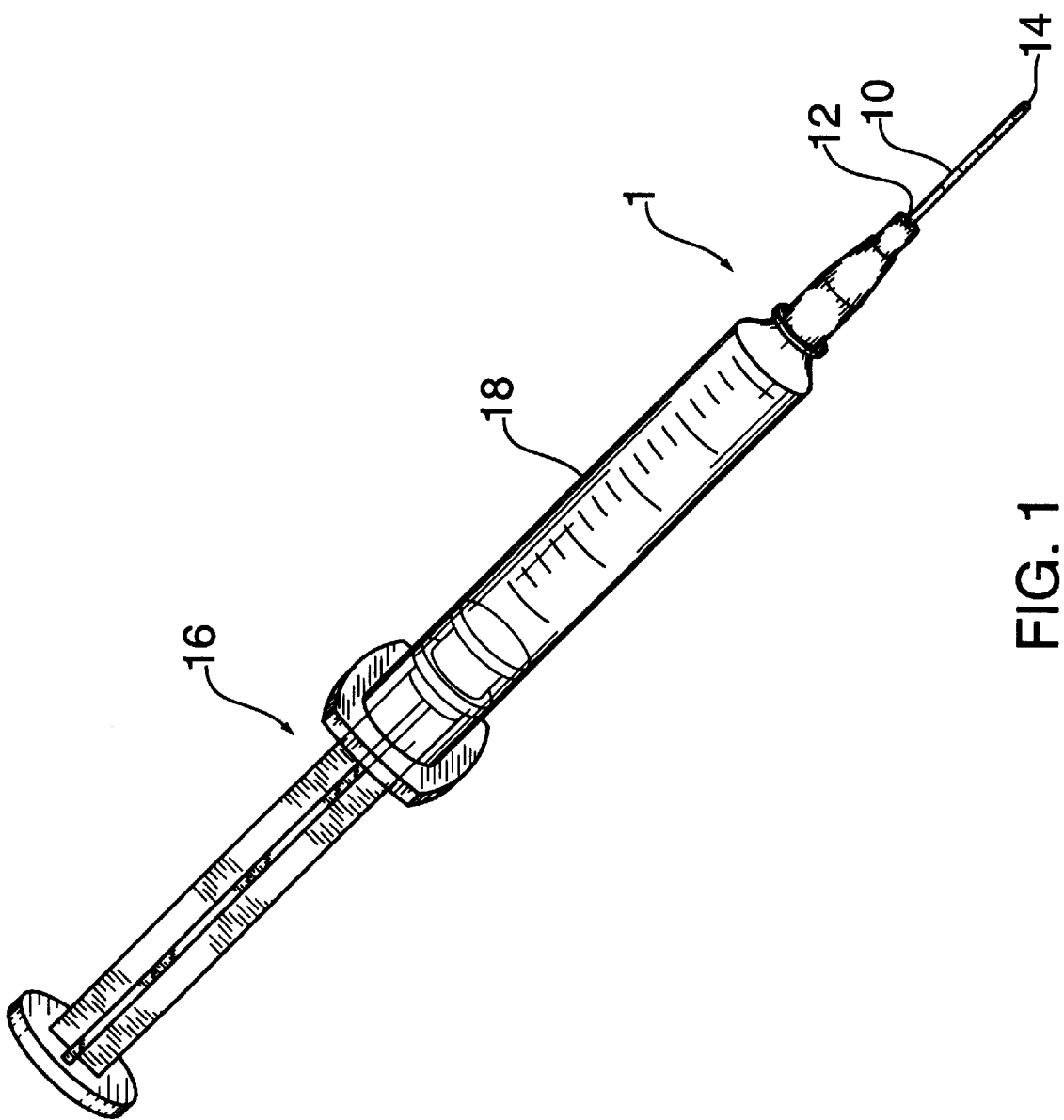
FIG. 1 is a perspective view of a syringe with a flexible needle thereon.

As shown in FIG. 1, the present invention is an endodontic syringe 1 with flexible needle for irrigating and delivering medication to intra-tooth canals during endodontic root canal treatment, including flexible hollow needle 10 extending between a proximal connection end 12 and a distal fluid discharge end 14. Flexible syringe needle 10 has plunger means 16 for introducing irrigating or medicating fluid through conduct 18 into hollow needle 10. Plunger means 16 is removably connected to proximal connection end 12 of flexible needle 10.

Alternatively, a disposable flexible syringe needle may have the needle and plunger means integrally connected, so that the entire syringe is disposable after use.

Figure 2:
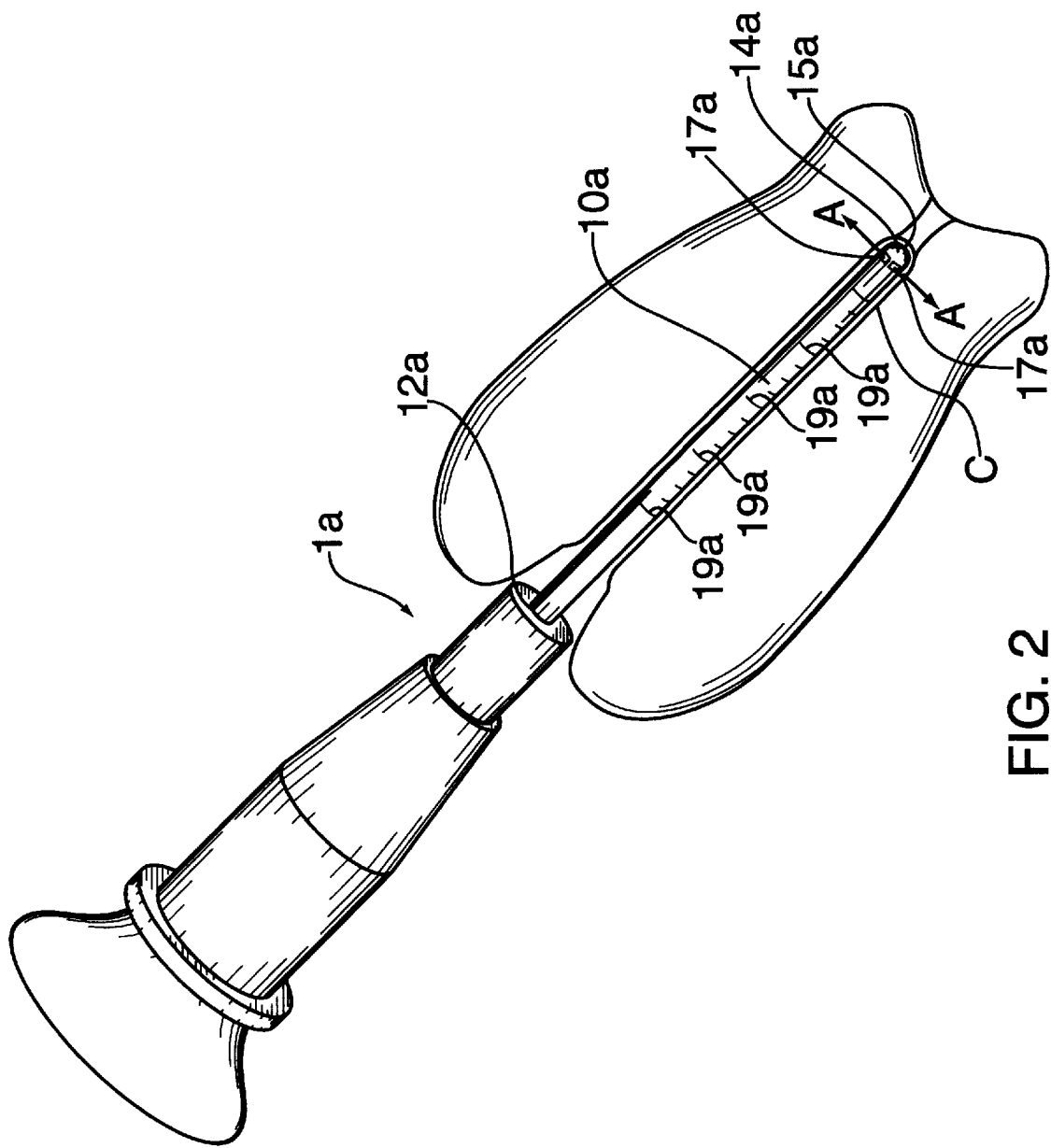
FIG. 2 is a closeup detail view of the flexible needle as in FIG. 1, with optional lateral side ports and measurement markings thereon, shown within a tooth canal.

As shown in FIG. 2, in another embodiment, endodontic syringe 1a needle for irrigating and delivering medication to intra-tooth canal C includes a flexible hollow needle 10a extending between a proximal connection end 12a and a distal end 14a having a sealed tip 15. Flexible syringe needle also has plunger means (not shown) for introducing irrigating or medicating fluid into said hollow needle 10a wherein the plunger means is removably connected to proximal connection end 12a of flexible needle 10a.

Figure 3:
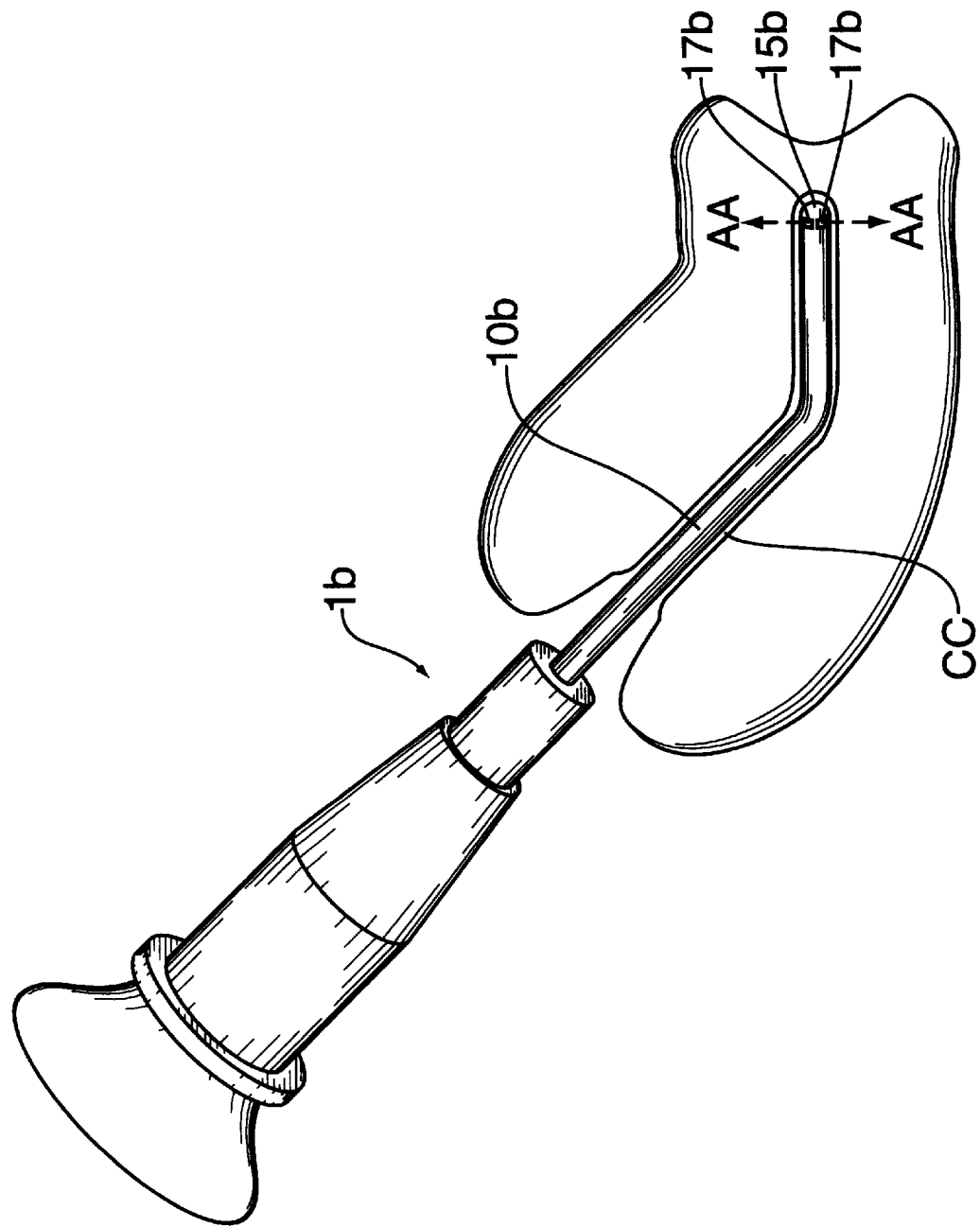
FIG. 3 is a closeup detail view of a curvilinear orientation of a flexible needle.

Flexible syringe needle boa may have a substantially straight-line shape as in FIG. 2, or a curvilinear shape as with flexible needle 10b of syringe 1b of FIG. 3. Furthermore, if flexible needle 10a is straight, it bends while encountering a curved tooth canal within a tooth, such as a canal.

Flexible syringe needles 10a, 10b preferably have at least one laterally placed fluid dispensing port, such as a plurality of ports 17a or 17b at a predetermined distance from sealed tip 15a or 15b for laterally dispensing fluid, such as in the direction of arrows "A" of "AA" shown. Dispensing ports 17a or 17b are disposed substantially at sealed tips 15a or 15b.

As shown in FIG. 4 flexible syringe needle 10c of syringe 1c may have dispensing ports as lateral side ports dispensing fluid substantially transverse to a longitudinal axis of flexible syringe needle 10c, or a plurality of longitudinally extending, spaced apart lateral side ports 17c wherein the plurality of lateral side ports 17c extend between the fluid discharge end 15c and connecting end 12c.

The plurality of lateral side ports 17c may extend in a longitudinally spaced apart relationship between end 15c and connecting end 12c.

As also shown in FIG. 3, if flexible syringe needle 10b is curved, dispensing ports 17b may be disposed substantially in the curved portion of flexible needle 10b In addition the tip 15b of flexible syringe needle 10b may have a sealed tip which is tapered.

As shown in FIG. 5, flexible syringe needle 10d of syringe 1d may have at least one dispensing port such as a plurality of micropores 17d between tip end 15d and connecting end 12d of needle 10d.

As also shown in FIG. 2, flexible syringe needle 10a may have at least one measuring marking 19a on an exterior surface thereof to visually verify a working length thereof. The at least one measuring marking 19a on an exterior surface thereof comprises a plurality of measuring marking 19a thereon.

As shown in FIG. 6, syringe 1e may have flexible needle 10e with a back flow means 21e for directing fluid discharged therefrom in a direction from an inner apical end of said tooth canal towards an outer coronal end, in the direction of arrows D shown, such as a lengthwise extending groove 21e within an outer surface of flexible syringe needle 10e.

Figure 8:
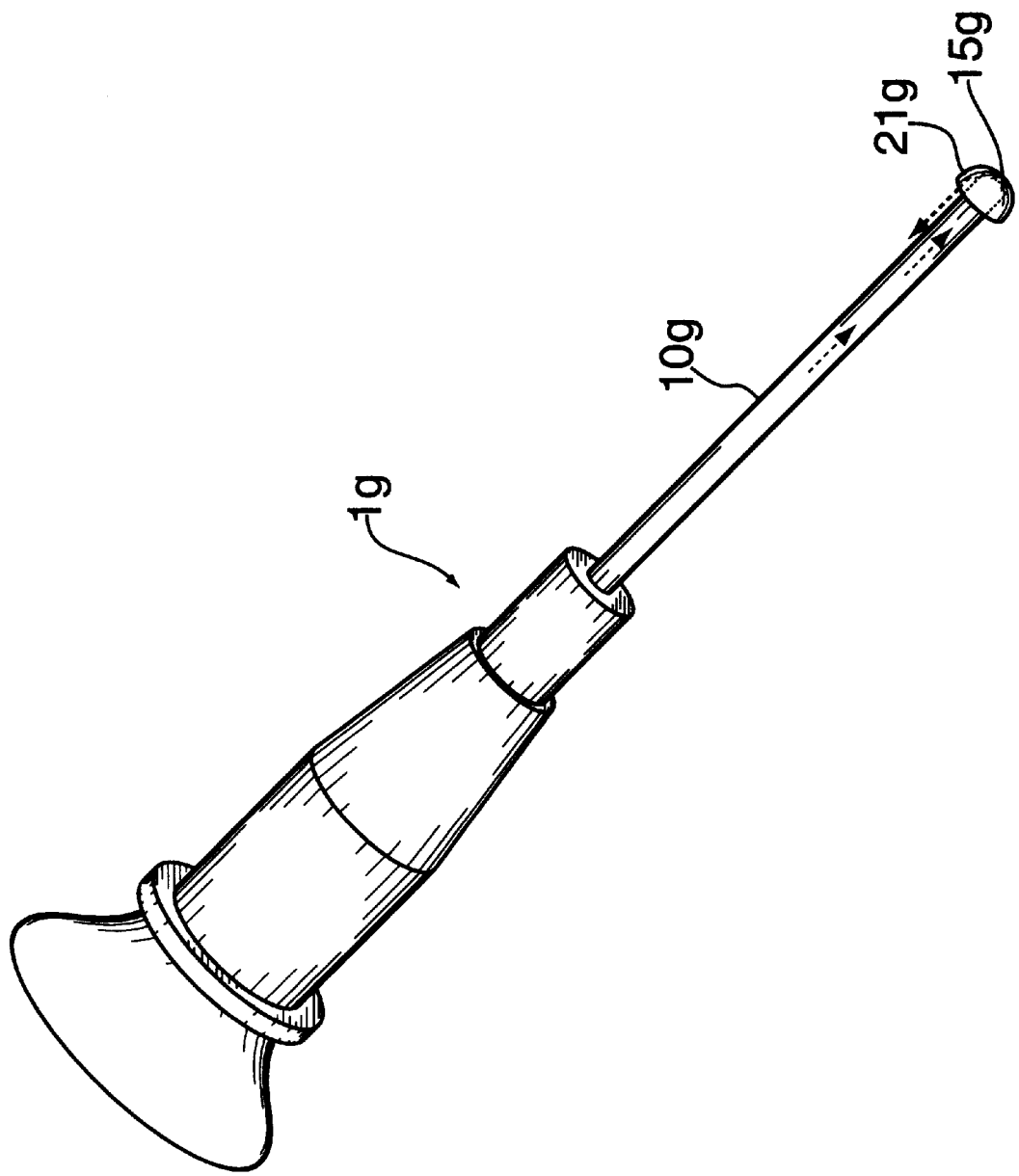
FIG. 8 is a closeup detail view of another embodiment for a flexible needle with a back flow enhancer and, FIG. 9 is a flow chart for a flexible needle and syringe connected to an electronic pump, wherein fluid flow pressure and temperature are electronically controlled.

Lengthwise extending groove 21e within an outer surface of flexible syringe needle 10f may be a straight channel, as shown in FIG. 7, with an axially positional discharge end 15f, or may be a curvilinear channel such as a spiral (not shown). Alternatively, as shown in FIG. 8, back flow means 21g of needle 10g of syringe 1g may be a concave barrier 21g at the bottom 15g of needle 10g, to direct fluid flow backwards.

Figure 9:
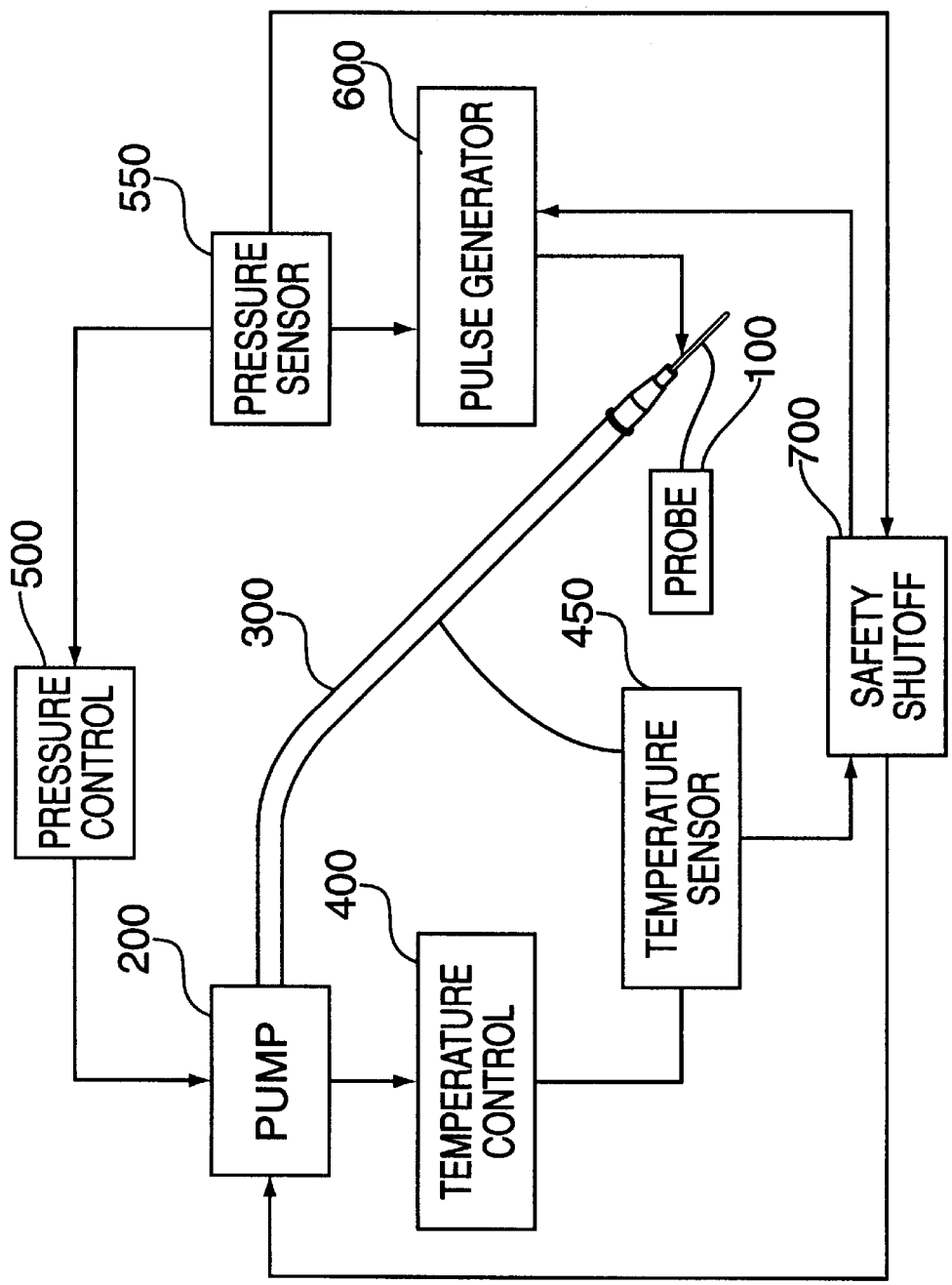

For sophisticated use, as shown in FIG. 9, the flexible syringe needle 1h may have electronic measuring probe 100 attached thereto for sensing physical conditions for measurement or fluid flow control.

Also in FIG. 9, flexible syringe needle 10h is connectable to a remote pump 200 for directing fluid at a controlled rate to the tooth canal through conduit 300, which connects pump 200 to flexible syringe needle 1h.

Pump 200 is preferably typically those used in intravenous pumps, wherein the solution being pumped is isolated from any metal pumping and transporting parts, to prevent corrosion of the solution, especially if the solution includes chelating agents susceptible to deterioration upon exposure to metal.

The pump has a temperature control that can heat a solution containing chelating agents to increase their effectiveness. The pump also has a pressure control to increase pressure to allow flow through smaller gauge needles and for safely avoiding excess pressure.

Flexible syringe needle 1h may have temperature control means 400 communicating with temperature sensor 450 for controlling the temperature of the fluid discharged from flexible needle 10h.

Flexible syringe needle 10h may also have a pressure control means 500 communicating with pressure sensor 550 for controlling the flow pressure of the fluid discharged from flexible needle 10h.

Remote pump 200 for directing fluid at a controlled rate to the tooth canal may also communicate with a pulse activating means 600, such as a fluid pulse generator to deliver fluid under intermittent pulses for discharging lodged debris from within the tooth canal. Pump 200 may have an auxiliary ultrasonic vibratory means for removing debris from within the tooth canal.

Furthermore, flexible syringe needle 10h may have a feedback safety shutoff means 700 for shutting off the flow of fluid from flexible needle 10h if at least one predetermined threshold condition is met, such as a predetermined fluid flow pressure or temperature. optionally, the flexible syringe needle 10h may be a plurality of user selectable needles (not shown) having a range of aperture sizes for user determination of fluid dispensing flow rate according to user selected fluid dispensing aperture size.

To be flexible, flexible needle 10h is made of plastics, such as polyethylene or polypropylene. Needle 10h may also be a silicone, or a flexible metal, such as nitinol.

In another embodiment a flexible syringe needle may be a collapsible fluid-inflatable elongated dispensing container (not shown) made of a pharmaceutically suitable material, wherein the flexible needle assumes its shape when filled with fluid from a means for introducing irrigating or medicating fluid into the hollow needle.

In yet another embodiment, a flexible syringe needle may include a chain-like plurality (not shown) of articulated rigid segments having a fluid delivery tube running longitudinally there through, wherein the segments and tube are comprised of a pharmaceutically suitable material.

As shown in FIG. 7, the flexible syringe needle may further include at least one bristle fiber 23 or a plurality of fibers 23, extending transverse from said needle for cleaning debris within the tooth canal. This feature is not limited to the embodiment shown in FIG. 7, and can be added to any of the embodiment showing FIGS. 1–9.

It is finally noted that other modifications may be made to the present invention, without departing from the scope of the invention, as noted in the appended claims.

We claim:

1. An endodontic flexible syringe needle for negotiating the curves of a tooth canal, and for irrigating and delivering medication to intra-tooth canals, comprising:

a flexible hollow needle extending between a proximal fluid flow connection end and at least one distal fluid dispensing port, said hollow needle being sufficiently flexible over its whole length to conform to the shape of a tooth canal and removably connected to said proximal fluid flow connection end permitting replacement of said hollow needle, said flexible syringe needle having means for introducing irrigating or medicating fluid into said hollow syringe needle, said flexible hollow needle being made from a material capable of flexing back by being deformable from a first predetermined configuration during insertion into said tooth canal and returnable to said first predetermined configuration upon removal from the tooth canal.

2. The endodontic flexible syringe needle for irrigating and delivering medication to intra-tooth canals, as in claim 1 further comprising:

said flexible hollow needle having a sealed tip, said needle having at least one fluid dispensing port at a predetermined distance from said sealed tip for dispensing fluid.

3. The flexible syringe needle of claim 1 wherein said needle comprises a substantially straight-line shape.

4. The flexible syringe needle of claim 1 wherein said needle comprises a substantially curvilinear shape.

5. The flexible syringe needle of claim 1, wherein said at least one dispensing port is disposed substantially at said sealed tip.

6. The flexible needle as in claim 1 wherein said at least one fluid dispensing port is a lateral side port dispensing fluid substantially transverse to a longitudinal axis of said flexible syringe needle.

7. The flexible needle as in claim 6 wherein said at least one fluid dispensing port is a plurality of lateral side ports.

8. The flexible needle as in claim 6 wherein said plurality of lateral side ports extend between said fluid dispensing end and said connecting end.

9. The flexible needle as in claim 6 wherein said plurality of lateral side ports extend in a longitudinally spaced apart relationship between said fluid dispensing end and said connecting end.

10. The flexible syringe needle of claim 1 wherein said at least one dispensing port is disposed substantially in the curved portion of said needle.

11. The flexible syringe needle of claim 2, wherein said sealed tip is tapered.

12. The flexible syringe needle of claim 1, wherein said at least one dispensing port comprises a plurality of micropores.

13. The flexible syringe needle as in claim 1 further comprising at least one measuring marking on an exterior surface thereof to visually verify a working length thereof.

14. The flexible syringe needle as in claim 13 wherein said at least one measuring marking on an exterior surface thereof comprises a plurality of measuring markings thereon.

15. The flexible syringe needle as in claim 2 further comprising a means for directing fluid dispensing therefrom in a direction from an inner apical end of said tooth canal towards an outer coronal end.

16. The flexible syringe needle as in claim 15 wherein said means for directing fluid dispensing therefrom in a direction from an inner apical end of said tooth canal towards an outer coronal end comprises a lengthwise extending groove within an outer surface of said flexible syringe needle.

17. The flexible syringe needle as in claim 16 wherein said lengthwise extending groove within an outer surface of said flexible syringe needle comprises a straight channel.

18. The flexible syringe needle as in claim 16 wherein said lengthwise extending groove within an outer surface of said flexible syringe needle comprises a curvilinear channel.

19. The flexible syringe needle as in claim 2 further comprising an electronic measuring probe attached thereto.

20. The flexible syringe needle as in claim 19 wherein said electronic measuring probe includes a sensor for sensing physical conditions.

21. The flexible syringe needle as in claim 19 wherein said flexible needle syringe is connectable to a remote pump for directing fluid at a controlled rate to the tooth canal.

22. The flexible syringe needle as in claim 21 wherein said remote pump for directing fluid at a controlled rate to the tooth canal further comprises a conduit connecting said pump to said flexible syringe needle.

23. The flexible syringe needle as in claim 21 wherein said remote pump for directing fluid at a controlled rate to the tooth canal further comprises a temperature control means for controlling the temperature of the fluid dispensing therefrom.

24. The flexible syringe needle as in claim 21 wherein said remote pump for directing fluid at a controlled rate to the tooth canal further comprises a pressure control means for controlling the flow pressure of the fluid dispensing therefrom.

25. The flexible syringe needle as in claim 21 wherein said remote pump for directing fluid at a controlled rate to the tooth canal further comprises a pulse activating means to deliver said fluid under intermittent pulses for discharging lodged debris from within the tooth canal.

26. The flexible syringe needle as in claim 21 further comprising an ultrasonic vibratory means for removing debris from within the tooth canal.

27. The flexible syringe needle as in claim 21 further comprising a flat touch pad control panel.

28. The flexible syringe needle as in claim 21 wherein fluid contact surfaces therein are non-metallic.

29. The flexible syringe needle as in claim 21 wherein said remote pump for directing fluid at a controlled rate to the tooth canal further comprises a feedback safety shutoff means for shutting off the flow of fluid therefrom if at least one predetermined threshold conditions is met.

30. The flexible syringe needle of claim 1 wherein said flexible syringe needle comprises a plurality of user selectable needles having wherein said at least one dispensing port comprises a range of aperture sizes for user determination of fluid dispensing flow rate according to user selected fluid dispensing aperture size.

31. The flexible syringe needle of claim 1 wherein said flexible needle is comprised of plastic.

32. The flexible syringe needle of claim 31 wherein said flexible needle is comprised of polyethylene.

33. The flexible syringe needle of claim 31 wherein said flexible needle is comprised of polypropylene.

34. The flexible syringe needle of claim 1 wherein said flexible needle is comprised of a flexible metal alloy.

35. The flexible syringe needle of claim 34 wherein said flexible metal alloy is nitinol alloy.

36. The flexible syringe needle of claim 1, wherein said flexible needle is comprised of a collapsible fluid-inflatable elongated dispensing container made of a pharmaceutically suitable material; said flexible needle assuming its shape when filled with fluid from said means for introducing irrigating or medicating fluid into said hollow needle.

37. The flexible syringe needle of claim 1 wherein said flexible needle is comprised of a chain-like plurality of articulated rigid segments having a fluid delivery tube running longitudinally therethrough, said segments and tube being comprised of a pharmaceutically suitable material.

38. The flexible syringe needle of claim 15 wherein said means for directing fluid is a concave surface at said tip end of said needle.

39. The flexible syringe needle as in claim 1 further comprises at least one bristle fiber extending transverse from said needle for cleaning debris from within the tooth canal.

40. The flexible syringe needle as in claim 1 wherein said needle has a hollow shaft with a diameter approximately equal to predetermined I.S.O. diameters that approximate the size of files and reamers used to endodontically treat a tooth canal.

41. A flexible syringe needle for negotiating through curved body cavities and for irrigating and delivering medications to said body cavities, comprising:

a flexible hollow needle insertable within a body cavity, said flexible syringe needle extending between a proximal fluid flow connection end and at least one dispensing port, said hollow needle being sufficiently flexible over its whole length to conform to the shape of a selected body cavity and removably connected to said proximal fluid flow connection end permitting replacement of said hollow needle, said flexible syringe needle having means for introducing irrigating or medicating fluid into said hollow syringe needle;

said flexible hollow needle being made of a material capable of flexing back by being deformable from a first predetermined configuration during insertion into the body cavity and returnable to said first predetermined configuration upon removal from the curved body cavity.

42. An endodontic flexible syringe needle in combination with a syringe for irrigating and delivering medication to an intra-tooth canal, comprising:

a flexible hollow needle extending from a proximal fluid flow connection end of said syringe, said hollow needle being sufficiently flexible over its whole length to conform to the shape of a tooth canal and removably connected to said syringe permitting replacement of said hollow needle, said syringe having means for introducing irrigating or medicating fluid into said hollow syringe needle, and said flexible hollow needle being made from a material capable of flexing back to its original shape after being removed from said canal.

* * * * *